(12) United States Patent
Hantschel et al.

(10) Patent No.: US 8,287,744 B2
(45) Date of Patent: Oct. 16, 2012

(54) CAPILLARY-CHANNEL PROBES FOR LIQUID PICKUP, TRANSPORTATION AND DISPENSE USING STRESSY METAL

(75) Inventors: Thomas Hantschel, Menlo Park, CA (US); David K. Fork, Los Altos, CA (US); Eugene M. Chow, Mountain View, CA (US); Dirk De Bruyker, Palo Alto, CA (US); Michel A. Rosa, Brisbane (AU)

(73) Assignee: Palo Alto Research Center Incorporated, Palo Alto, CA (US)

( * ) Notice: Subject to any disclaimer, the term of this patent is extended or adjusted under 35 U.S.C. 154(b) by 156 days.

(21) Appl. No.: 12/775,452

(22) Filed: May 6, 2010

(65) Prior Publication Data
US 2010/0213161 A1 Aug. 26, 2010

Related U.S. Application Data

(62) Division of application No. 11/267,762, filed on Nov. 3, 2005, now Pat. No. 7,749,448, which is a division of application No. 10/213,059, filed on Aug. 5, 2002, now Pat. No. 7,241,420.

(51) Int. Cl.
*B44C 1/22* (2006.01)
*B32B 38/10* (2006.01)
*C23C 14/34* (2006.01)

(52) U.S. Cl. ......... 216/2; 216/11; 156/247; 204/192.32; 204/192.35

(58) Field of Classification Search ............... None
See application file for complete search history.

(56) References Cited

U.S. PATENT DOCUMENTS

| | | | |
|---|---|---|---|
| 3,842,189 A | 10/1974 | Southgate | |
| 5,063,081 A | 11/1991 | Cozzette et al. | |
| 5,200,248 A | 4/1993 | Thompson et al. | |
| 5,613,861 A | 3/1997 | Smith et al. | |
| 5,635,750 A | 6/1997 | Schlaak et al. | |
| 5,909,230 A | 6/1999 | Choi et al. | |
| 5,914,218 A | 6/1999 | Smith et al. | |
| 6,101,946 A | 8/2000 | Martinsky | |
| 6,213,789 B1 | 4/2001 | Chua et al. | |
| 6,396,966 B1 | 5/2002 | Lewis et al. | |

(Continued)

FOREIGN PATENT DOCUMENTS

JP 07-103996 4/1995
(Continued)

OTHER PUBLICATIONS

Belaubre et al. "Cantilever-based microsystem for contact and non-contact deposition of picoliter biological samples," Sensors and Actuators A 110 (2004), pp. 130-135.

Chinthakindi et al. "Electrostatic Actuators with Intrinsic Stress Gradient, I. Materials and Structures," Journal of the Electrochemical Society, vol. 149, No. 8, Jun. 14, 2002, pp. H139-H145.

(Continued)

*Primary Examiner* — Allan Olsen
(74) *Attorney, Agent, or Firm* — Bever, Hoffman & Harms, LLP; Patrick T. Bever

(57) ABSTRACT

Fluidic conduits, which can be used in microarraying systems, dip pen nanolithography systems, fluidic circuits, and microfluidic systems, are disclosed that use channel spring probes that include at least one capillary channel. Formed from spring beams (e.g., stressy metal beams) that curve away from the substrate when released, channels can either be integrated into the spring beams or formed on the spring beams. Capillary forces produced by the narrow channels allow liquid to be gathered, held, and dispensed by the channel spring probes. Because the channel spring beams can be produced using conventional semiconductor processes, significant design flexibility and cost efficiencies can be achieved.

19 Claims, 16 Drawing Sheets

U.S. PATENT DOCUMENTS

| | | |
|---|---|---|
| 6,668,628 B2 | 12/2003 | Hantschel et al. |
| 6,766,817 B2 | 7/2004 | da Silva |
| 7,241,420 B2 | 7/2007 | Hantschel et al. |
| 2002/0055282 A1 | 5/2002 | Eldridge et al. |
| 2002/0063212 A1 | 5/2002 | Mirkin et al. |
| 2006/0057031 A1 | 3/2006 | Hantschel et al. |
| 2008/0147346 A1 | 6/2008 | Eby et al. |
| 2010/0213161 A1 | 8/2010 | Hantschel et al. |

FOREIGN PATENT DOCUMENTS

| | | |
|---|---|---|
| JP | 2001-505640 | 4/2001 |
| JP | 2001-326259 | 11/2001 |
| WO | WO9826179 | 6/1998 |
| WO | 00/25922 A2 | 5/2000 |
| WO | WO0133614 A1 | 5/2001 |
| WO | WO03097238 A1 | 11/2003 |

OTHER PUBLICATIONS

Datta, M. "Microfabrication by Electrochemical Metal Removal," IBM J. Res. Dev., vol. 42, No. 4, Sep. 4, 1998, pp. 655-669.

Lang, W. "Silicon microstructuring technology," Materials Science and Engineering, vol. 17, No. 1, Sep. 1, 1996, pp. 1-55.

Lee et al. "A practical microgripper by fine alignment, eutectic bonding and SMA actuation," Sensors and Actuators A, vol. 54, No. 1-3, Jun. 1, 1996, pp. 755-759.

Lewis et al. "Fountain pen nanochemistry: Atomic force control of chrome etching," Applied Physics Letters, vol. 75, No. 17, Oct. 25, 1999, pp. 2689-2691.

Piner et al. "Dip-Pen Nanolithography," Science, vol. 283, Jan. 29, 1999, pp. 661-663.

Zhang et al. "A MEMS Nanoplotter with High-Density Parallel Dip-Pen Nanolithography Probe Arrays," Institute of Physics Publishing, Nanotechnology 13 (2002) pp. 212-217.

Eby, specification of U.S. Appl. No. 60/367,514, filed Mar. 27, 2002.

_US 8,287,744 B2_

CAPILLARY-CHANNEL PROBES FOR LIQUID PICKUP, TRANSPORTATION AND DISPENSE USING STRESSY METAL

RELATED APPLICATIONS

This application is a divisional of U.S. patent application Ser. No. 11/267,762, entitled "Capillary-Channel Probes For Liquid Pickup, Transportation And Dispense Using Stressy Metal" filed Nov. 3, 2005, now U.S. Pat. No. 7,749,448, which is a divisional of U.S. patent application Ser. No. 10/213,059, entitled "Capillary-Channel Probes For Liquid Pickup, Transportation And Dispense Using Stressy Metal" filed Aug. 5, 2002, now U.S. Pat. No. 7,241,420.

FIELD OF THE INVENTION

This invention relates generally to microfluidic devices, and more particularly to liquid handling probes for such devices.

BACKGROUND OF THE INVENTION

The developing field of microfluidics deals with the manipulation and measurement of exceedingly small liquid volumes—currently down to the nanoliter, or even picoliter range. For example, modern analytical integrated circuits (ICs), such as "system on a chip" (SOC) or "lab on a chip" (LOC) biochips, can analyze solutions that are deposited directly on the chip surface. Typically, the surface of an analytical IC will include an array of analysis locations so that multiple analyses can be performed simultaneously. A "microarraying" system that includes a biochip is extremely useful for genetics research because of the substantial improvements in efficiency provided by this parallel analysis capability. To maximize the number of analysis locations (and therefore the number of analyses that can be performed at one time), the size of each analysis location on the biochip is minimized. To ensure that the biological solution from one analysis location does not flow into a different analysis location, an array (often referred to as a "microarray") of microfluidic "printing tips" is used to dispense a precise volume of the biological solution at each analysis location.

FIG. 1 is a perspective view of a conventional microarraying system 100, which includes a stage 110 for supporting a biochip 120, a microarray 130 mounted to an XYZ positioning subsystem 160, and a computer/workstation 170 that serves as both a system controller and a measurement data processor. Microarray 130 includes a plurality of printing tips 150 mounted in an array formation on a mounting base 140. XYZ positioning subsystem 160 moves microarray 130 in response to control signals provided by computer/workstation 170 to collect and dispense samples of test solutions in an array pattern on biochip 120. A channel 151 cut into the end of each printing tip 150 stores and dispenses tiny samples of the test solutions onto specific analysis locations on biochip 120. In this manner, each printing tip 150 acts as a microfluidic conduit—i.e., a transport pathway for microfluidic volumes of liquid. Biochip 120 then analyzes the samples in parallel and provides the results to computer/workstation 170 for further processing. As mentioned previously, this type of concurrent analysis greatly reduces the amount of time required to perform a set of experiments.

To ensure that test samples are accurately and evenly placed on biochip 120, printing tips 150 in microarray 130 must be made to extremely tight tolerances and must be precisely arranged in microarray 130. As the number of pins is increased to allow larger numbers of samples to be concurrently tested, the dimensional requirements only become stricter. As a result, the microarrays used in conventional microarraying systems are expensive and difficult to manufacture. For example, companies such as Oxford Lasers, Ltd. manufacture the metal pins used to dispense biological solutions in microarraying systems such as microarraying system 100 using techniques such as electro-discharge machining (EDM) and copper-vapor-laser (CVL) micro-machining. The minimum channel width in such pins is roughly 10 µm, with each pin being fabricated individually and taking up to 30 minutes to complete. Once pin formation is complete, the pins still must be assembled into the high-precision microarray, which adds additional time and expense to the manufacturing process. This low production throughput (Oxford Lasers, Ltd. is currently manufacturing about 1000 pins/months for BioRobotics) means that the final microarrays are extremely expensive. This in turn impacts testing throughput, since the high cost of the microarrays mandates that they be reused rather than replaced. Therefore, to prevent cross-contamination, the microarrays must be meticulously cleaned, which can be very time-consuming.

Even for microfluidic systems using a smaller number of printing tips, pin costs can be problematic. For example, FIG. 2 shows a perspective view of a dip pen nanolithography (DPN) system 200. DPN system 200 includes a stage 210 for supporting a wafer 220, a micropen assembly 230 mounted to an XYZ positioning subsystem 260, and a computer/workstation 270 that serves as a system controller. Micropen assembly 230 includes a printing tip 250 mounted in a mounting base 240. XYZ positioning subsystem 260 moves micropen assembly 230 in response to control signals provided by computer/workstation 270 to print a desired pattern on wafer 220. A channel 251 is cut into printing tip 250 to allow the printing tip to act as a microfluidic conduit and apply a print solution onto wafer 220. This type of micropen-based lithography can allow more complex and detailed patterns to be printed than would be possible using conventional lithography techniques. However, as with microarraying systems, the difficulties in fabrication and the high cost associated with the metal pins used in micropen assemblies limit the usefulness of current DPN systems, for much the same reasons as were previously described with respect to conventional microarraying systems. Alternative DPN systems, such as the lithographically-formed planar beams with perpendicular printing tips is described in "A MEMS Nanoplotter with High-Density Parallel Dip-Pen Nanolithography Probe Arrays", Zhang et al., *Nanotechnology*, v13 (2002), pp. 212-217, present other difficulties, as the flat configuration of the planar beams can consume significant die area, thereby limiting the printing tip density, and the printing tips themselves require delicate sharpening operations that can adversely impact both yield and cost.

What is needed is a microfluidic conduit that can be produced and formed into microfluidic devices such as microarrays and micropen assemblies without the manufacturing difficulties and high costs associated with conventional metal pins.

SUMMARY OF THE INVENTION

The present invention is directed towards fluidic systems that are formed using stress-engineered spring material (e.g., "stressy metal") films. The spring material films are formed into channel spring probes, each of which includes a spring beam having a fixed end (anchor portion) attached to a substrate and a free section bending away from the substrate, and a channel or multiple channels in or on each spring beam, parallel to the curvature of the spring beam. The channel(s) in and/or on the spring beam allow the channel spring probe to act as a fluidic conduit. The channel and tip configurations (referred to in the aggregate as "fluid handling features") of the channel spring probe can be designed to enhance the ability of the channel spring probe to store, draw fluid into, or dispense fluid from the channel(s). A channel spring probe or multiple channel spring probes can be used in any system requiring a fluidic conduit that provides out-of-plane fluid handling capabilities; e.g., a microarraying system, a DPN system, or a fluidic circuit.

Channel spring probes of the present invention are produced by forming (e.g., sputtering, chemical vapor deposition, or electroplating) a spring material (e.g., metal, silicon, nitride, or oxide) onto a substrate while varying the process parameters (e.g., pressure, temperature, and applied bias) such that a stress-engineered spring material film is formed with an internal stress gradient in the growth direction (i.e., normal to the substrate). The spring material film is then etched to form an elongated island of spring material, and an anchor portion (fixed end) of the spring material island is then masked. The unmasked portion of the spring material island is then "released" by removing (etching) a sacrificial material located under the unmasked portion, forming a spring beam curving away from the substrate. In one embodiment, the sacrificial material removed during the release process is a separate "release" material layer (e.g., Si, SiNx, SiOx, or Ti) that is formed between the substrate surface and the spring material film. In another embodiment, the spring material film is formed directly on the substrate (e.g., silicon or quartz), and the substrate itself is etched during the release process. The released portion of the spring beam bends away from the substrate as the internal stress gradient of the spring material film relaxes, while the anchor portion remains secured to the substrate. By controlling the internal stress gradient of the spring material film, along with other spring beam characteristics (e.g., thickness, length, etc.), a desired curvature can be achieved.

According to another embodiment of the invention, a substrate is coated with resist and patterned to define the channel spring probe area. A material stack (including release layer and spring material film) is then deposited over the entire substrate. A lift-off step (e.g., submersion in acetone and applied ultrasonic agitation) is then used to remove the material outside the channel spring probe area. The advantage of the lift-off process is that it works with nearly any spring material, whereas the etching process allows only for spring materials that etch well.

Note that according to an embodiment of the invention, fluid handling features can be formed directly in the original spring material island, so that once the free portion is released from the substrate, the desired fluid handling features are already incorporated into the spring beam. In such a case, the channel spring probe is defined by the spring beam itself. Alternatively, the spring beam can be formed "blank" (i.e., having no integrated fluid handling features), with additional processing used to form channel structures on the surface(s) of the spring beam. In this case, the channel spring probe includes both the spring beam and the additional channel structures. Note that the additional processing operations that foam the channel structures can be performed either before or after release of the free portion of the spring material island from the substrate.

The channel spring probes of the present invention provide several advantages over conventional metal pins. For example, dispensing assemblies, such as microarrays or micropen assemblies, made using spring material technology can be manufactured much more cheaply than their conventional counterparts, since thousands of channel spring probes can be manufactured simultaneously using common fabrication methods such as lithography, sputtering and plating (versus metal pins that must be individually produced).

Furthermore, the channel spring probes can be formed in the desired array pattern, eliminating the time-consuming and delicate assembly process associated with conventional metal pin microarrays. This cost-effective manufacturing process may allow for microarrays that can be replaced between analysis runs, rather than being cleaned and reused. This can not only reduce test cycle time, but would also reduce the chances of cross-contamination between tests.

The spring material technology also allows for much smaller channel widths, limited only by the capabilities of the lithography and/or plating processes. For example, while metal pins may have a minimum channel width of 10 µm, channel spring probes can be readily formed with 1 µm channels. In addition, the smaller channel spring probes can be arranged in much denser arrays than can the larger metal pins.

Also, channel spring probes can be fabricated with almost any desired geometry, unlike metal pins, which are generally limited to a single channel. For example, channel spring probes could be produced having two or more channels each. Such multi-channel spring probes could be used, for example, to dispense mixtures of different biological or chemical solutions.

BRIEF DESCRIPTION OF THE DRAWINGS

These and other features, aspects and advantages of the present invention will become better understood with regard to the following description, appended claims, and accompanying drawings, where:

DETAILED DESCRIPTION OF THE DRAWINGS

Figure 1:
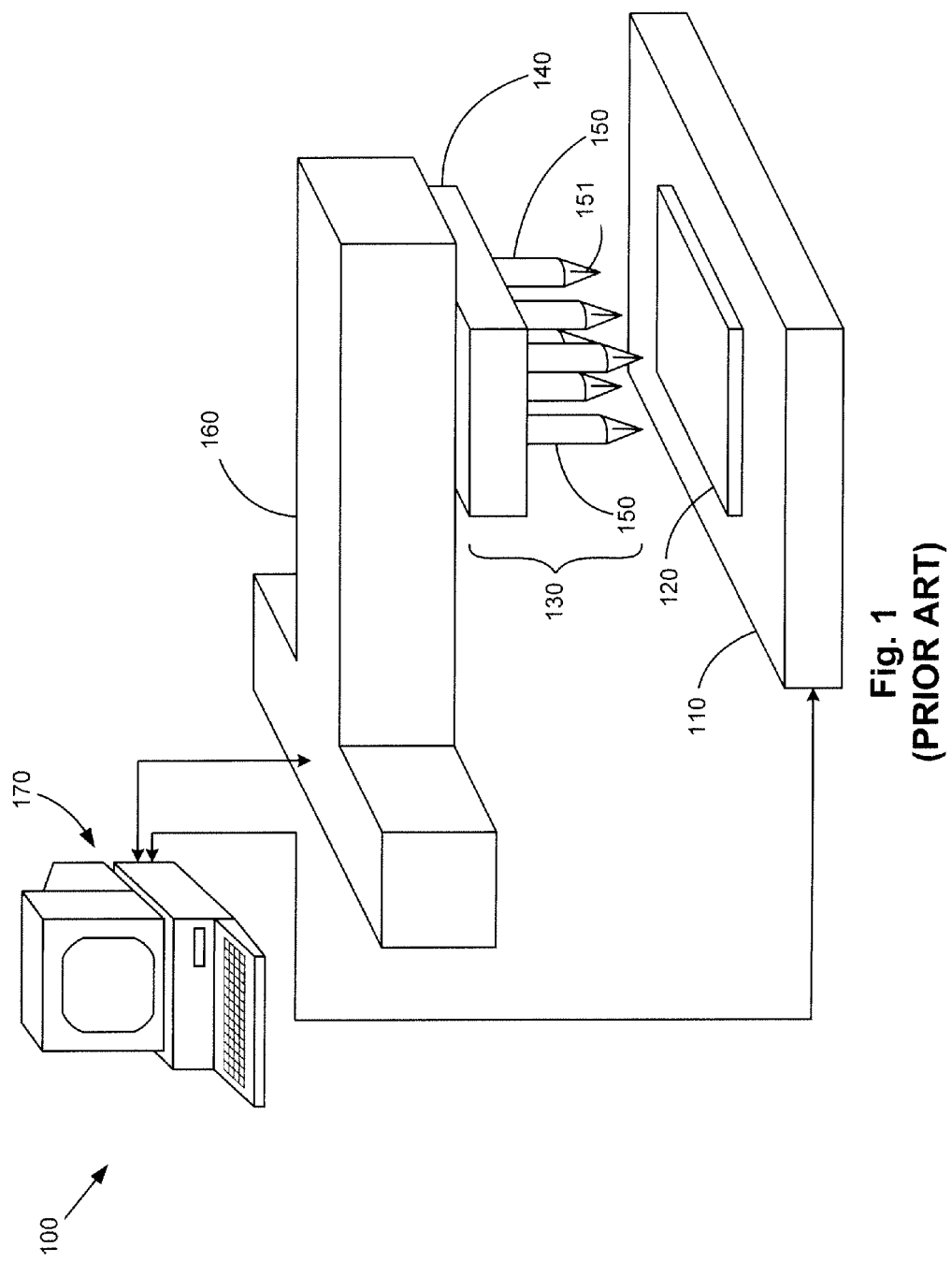
FIG. 1 is a perspective view showing a conventional microarraying system.
Figure 3A:
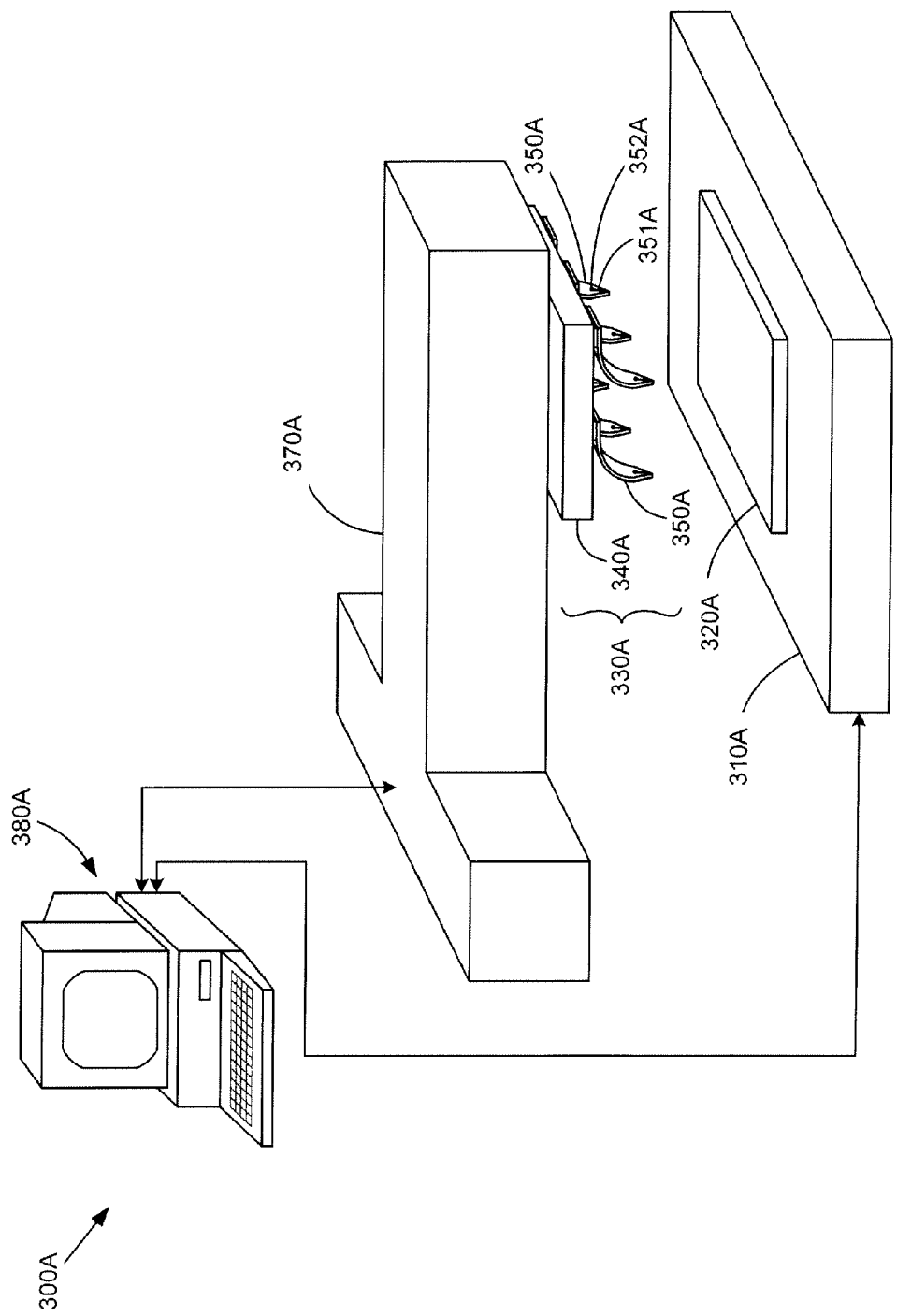
FIG. 3(A) is a perspective view showing a microarraying system using a channel spring probe dispensing assembly according to an embodiment of the invention.

FIG. 3(A) is a perspective view of a microarraying system 300A according to an embodiment of the invention. Microarraying system 300A includes a stage 310A for supporting an analytical IC 320A, a dispensing assembly 330A mounted to a positioning subsystem 370A, and a computer/workstation 380A that serves as both a system controller and a measurement data processor. Analytical IC 320A can comprise a biochip or any other type of IC providing surface-based analysis capabilities. Positioning subsystem 370A moves dispensing assembly 330A in response to control signals provided by computer/workstation 380A to collect and dispense samples of test solutions in an array pattern on analytical IC 320A. Note that positioning subsystem 370A can perform all the positional operations required to dispense the test samples on analytical IC 320A, or stage 310A could also include additional positioning capabilities for aligning analytical IC 320A and dispensing assembly 330A. Once the test samples have been deposited, analytical IC 320A performs a parallel analysis and provides the results to computer/workstation 380A for further processing. Microarraying system 300A is therefore substantially similar to microarraying system 100 shown in FIG. 1, except that metal pin-based microarray 130 is replaced with channel spring probe-based dispensing assembly 330A.

Dispensing assembly 330A includes a plurality of channel spring probes 350A in an array formation on a substrate 340A. As noted previously, channel spring probes 350A can be produced much more economically than printing tips 150 of microarraying system 100, and also can provide significantly improved accuracy and design flexibility. Each channel spring probe 350A includes a channel 351A that runs parallel to the curvature of the channel spring probe. Channels 351A are sized such that test solutions are pulled along the channel by capillary action. Therefore, when any of channel spring probes 350A is placed in contact with a liquid source, liquid is drawn in to channel 351A. Similarly, when the tip of any of channel spring probes 350A is placed in contact with the surface of analytical IC 320A, a quantity of liquid from channel 351A is deposited on biochip 320A. Between these liquid drawing and dispensing operations, the liquid is held in channel 351A by capillary and surface tension forces. An optional reservoir 352A formed in line with each channel 351A can increase the fluid storage capacities of channel spring probes 350A. Note that while each of channel spring probes 350A is depicted as having a tapered tip and a single channel, channel spring probes in accordance with embodiments of the invention can include any number of different tip and channel configurations, as will be discussed below. For example, each channel 351A in channel spring probes 350A could represent two channels, thereby allowing dispensing assembly 330A to dispense solution mixtures onto analytical IC 320A.

Figure 2:
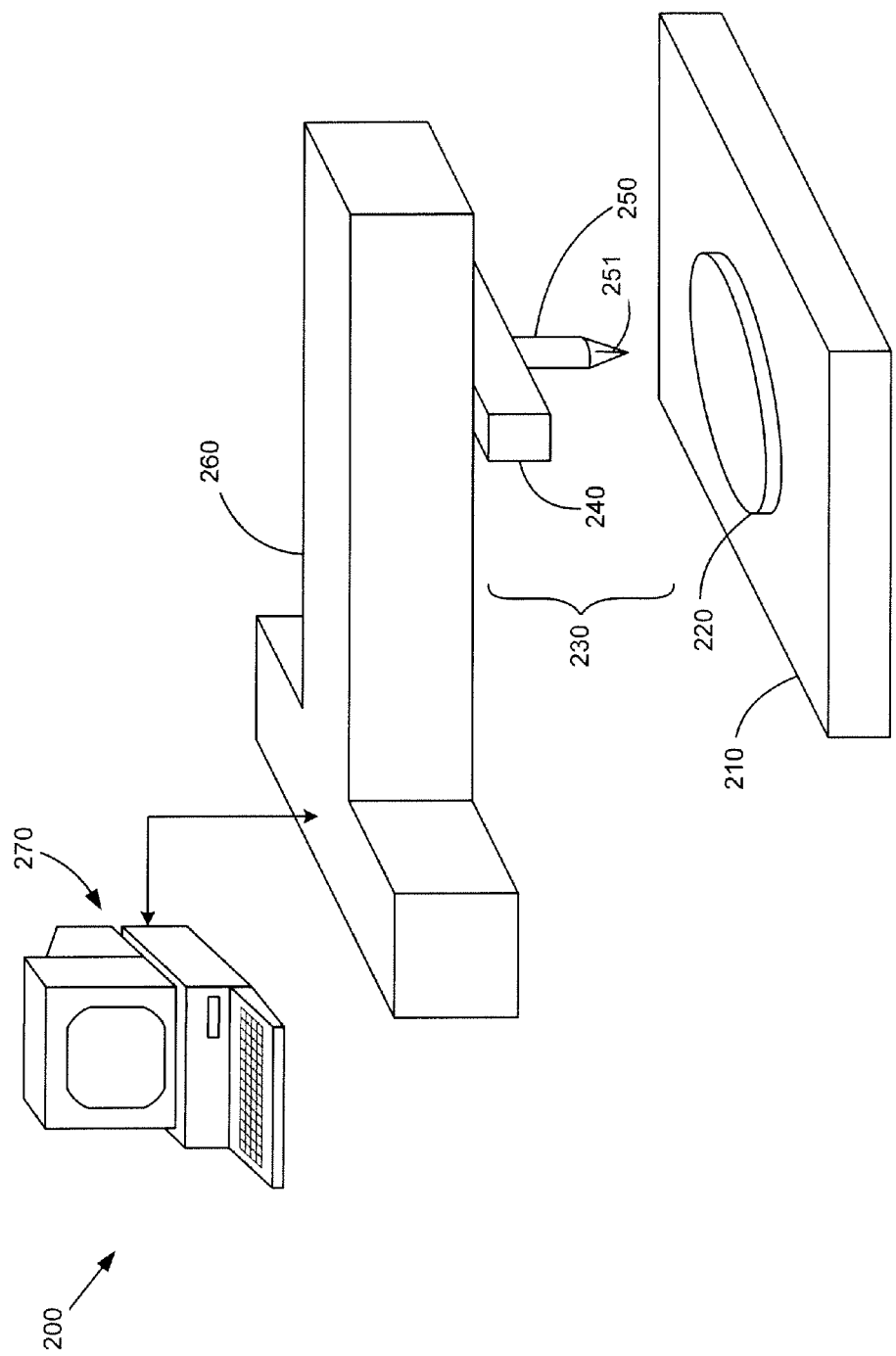
FIG. 2 is a perspective view showing a conventional DPN system.
Figure 3B:
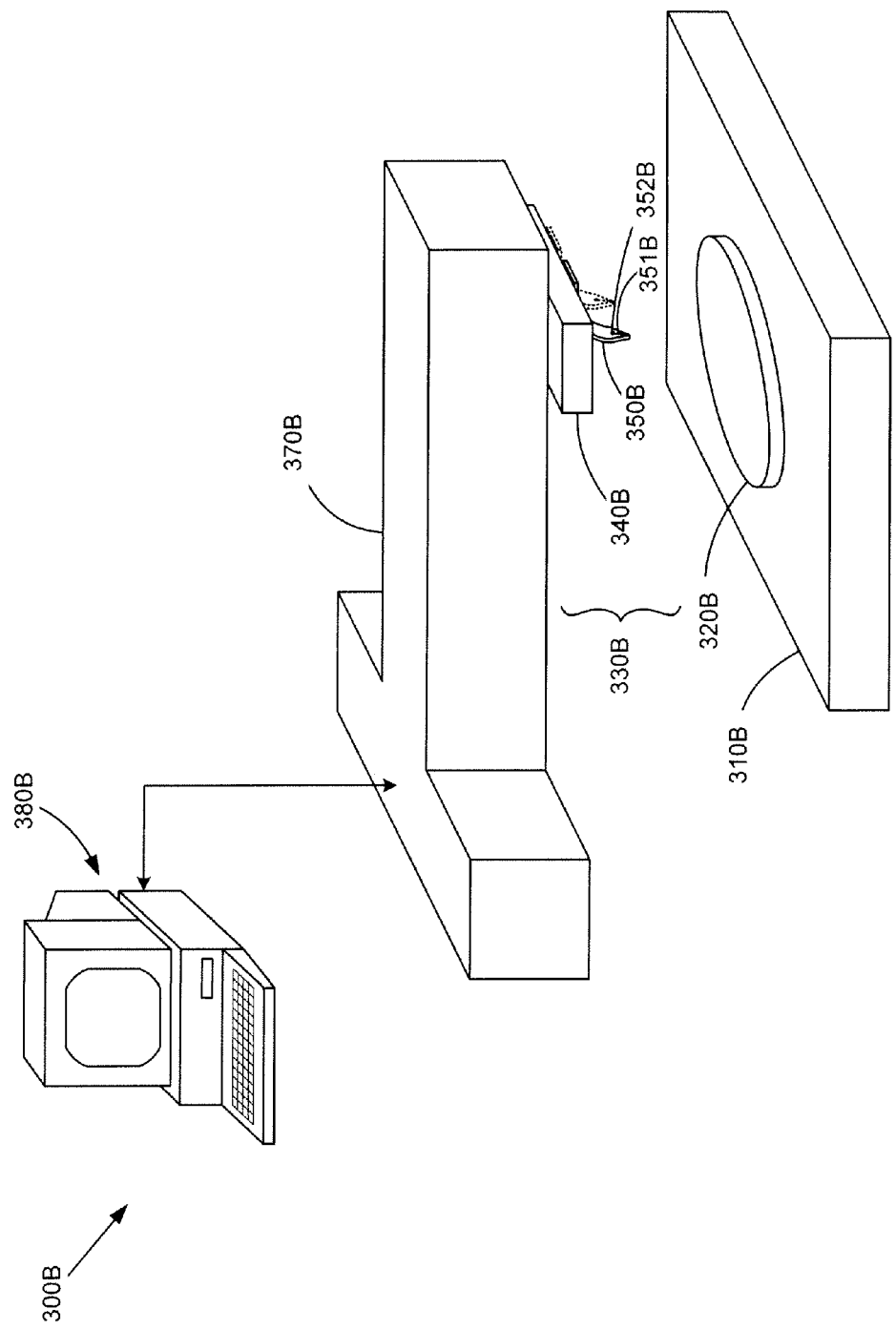
FIG. 3(B) is a perspective view showing a DPN system using a channel spring probe micropen assembly according to another embodiment of the invention.

FIG. 3(B) is a perspective view of a dip pen nanolithography (DPN) system 300B according to another embodiment of the invention. DPN system 300B includes a stage 310B for supporting a substrate 320B (such as a wafer), a micropen assembly 330B mounted to an XYZ positioning subsystem 370B, and a computer/workstation 380B that serves as a system controller. Micropen assembly 330B includes one or more channel spring probes 350B mounted in a mounting base 340B. XYZ positioning subsystem 370B moves micropen assembly 330E in response to control signals provided by computer/workstation 380B to print a desired pattern on wafer 320B. A channel 351B (parallel to the curvature of channel spring probe 350B) and an optional reservoir 352B in channel spring probe(s) 350B allow a print solution to be applied onto wafer 320B. DPN system 300B is therefore substantially similar to DPN system 200 shown in FIG. 2, except that metal pin-based micropen assembly 230 is replaced with channel spring probe-based micropen assembly 330B, once again providing the cost and design benefits associated with channel spring probes.

Figure 3C:
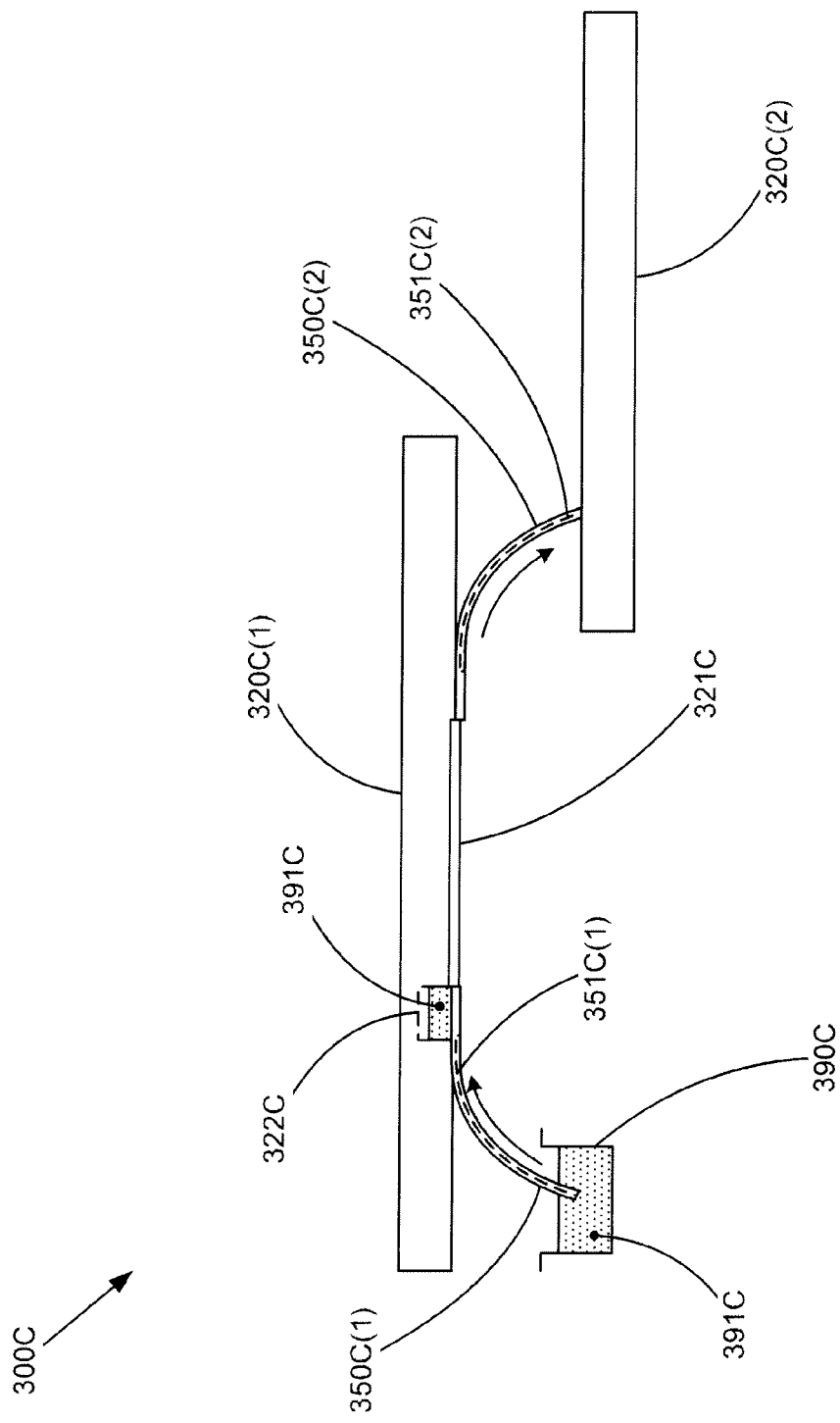
FIG. 3(C) is a perspective view showing a fluidic circuit using channel spring probe fluid interconnects according to another embodiment of the present invention.

FIG. 3(C) is a schematic view of a fluidic circuit 300C according to another embodiment of the invention. Circuit 300C includes fluidic devices 320C(1) and 320C(2), which can comprise any devices that use or incorporate microfluidic liquid volumes. For example, fluidic devices 320C(1) and 320C(2) can comprise biochips or other analytical integrated circuits (ICs) designed for fluid analysis. Fluidic device 320C(1) includes channel spring probes 350C(1) and 350C(2) for liquid collection and dispensing, respectively, a micro-channel network 321C for in-plane fluid routing, and an optional reservoir 322C for liquid storage. The free end of channel spring probe 350C(1) is placed in contact with a liquid 391C in an external supply container 390C, and capillary forces draw some of liquid 391C into a channel 351C(1) running parallel to the curvature of channel spring probe 350C(1). This drawn liquid can either be accumulated in optional reservoir 322C or passed to micro-channel network 321C. Micro-channel network 321C then routes the liquid to appropriate locations within fluidic device 320C(1), including to a channel 351C(2) in channel spring probe 350C(2). Channel 351C(2), which runs parallel to the curvature of channel spring probe 350C(2), allows the liquid to be dispensed from the tip of channel spring probe 350C(2) onto fluidic device 320C(2).

FIGS. 4(A) through 4(I) are simplified cross-sectional side views showing a general fabrication process utilized to produce channel spring probes such as channel spring probes 350A, 350B, and 350C, as shown in FIGS. 3(A), 3(B), and 3(C), respectively, according to another embodiment of the present invention.

Figure 4A:
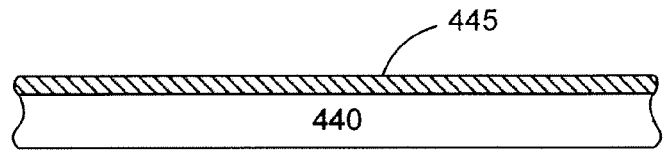
FIGS. 4(A), 4(B), 4(C), 4(D), 4(E), 4(F), 4(G), 4(H), and 4(I) are simplified cross-sectional side views showing a general fabrication process utilized to produce channel spring probes according to another embodiment of the present invention.

Referring to FIG. 4(A), the fabrication process begins by forming a release layer 445 on a wafer 440. Substrate 440 is formed from a selected substrate material (e.g., glass, quartz, silicon (Si), sapphire, aluminum oxide, or a suitable plastic). In one embodiment, release layer 445 includes one or more of Si, a silicon nitride composition (SiNx), a silicon oxide composition (SiOx), or titanium (Ti) that is deposited onto substrate 440. As described below, the release material is selected such that the channel spring probe remains connected via a portion of release layer 445 to substrate 440 after release. In an alternative embodiment, a separate anchor pad is separately formed adjacent to the release material that serves to connect the spring probe to substrate 440. While such a separately formed anchor pad may increase the strength of the channel spring probe/substrate connection, the formation of such an anchor pad would increase the number of process steps, thereby increasing the total probe manufacturing cost. In yet another alternative embodiment, the substrate material of substrate 440 may itself be used as the release layer (i.e., a separate release material deposition process is not used, and channel spring probe 450 is connected directly to substrate 440, as demonstrated by channel spring probes 350C(1) and 350C(2) in FIG. 3(C)).

Figure 4B:
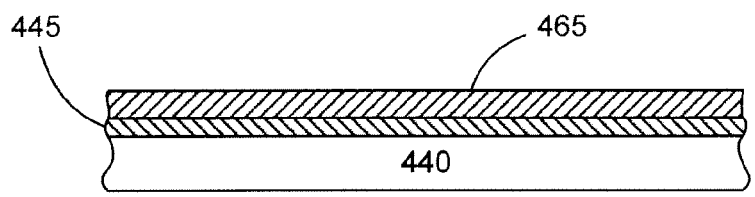
Figure 4C:
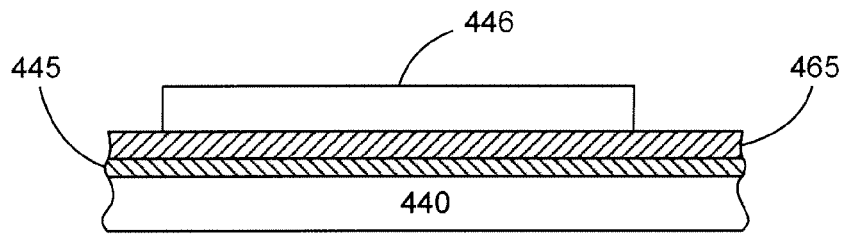

Next, as shown in FIG. 4(B), a stress-engineered (spring material) film 465 is formed on release layer 445 using known processing techniques such that film 465 includes internal stress variations in the growth direction. For example, in one embodiment, stress-engineered film 465 is formed such that its lowermost portions (i.e., adjacent to release material layer 410) have a higher internal compressive stress than its upper portions, thereby forming internal stress variations that cause a bending bias away from substrate 440. Methods for generating such internal stress variations in stress-engineered film 465 are taught, for example, in U.S. Pat. No. 3,842,189 (depositing two metals having different internal stresses) and U.S. Pat. No. 5,613,861 (e.g., single metal sputtered while varying process parameters), both of which being incorporated herein by reference. In one embodiment, stress-engineered film 465 includes one or more metals suitable for forming a spring structure (e.g., one or more of molybdenum (Mo), a "moly-chrome" alloy (MoCr), tungsten (W), a titanium-tungsten alloy (Ti:W), chromium (Cr), and nickel (Ni)). In other embodiments, stress-engineered film 465 is formed using Si, nitride, silicon oxide, carbide, or diamond. The thickness of stress-engineered film 465 is determined in part by the selected spring material, desired spring constant and shape of the final spring beam structure, as discussed in additional detail below.

Figure 5A:
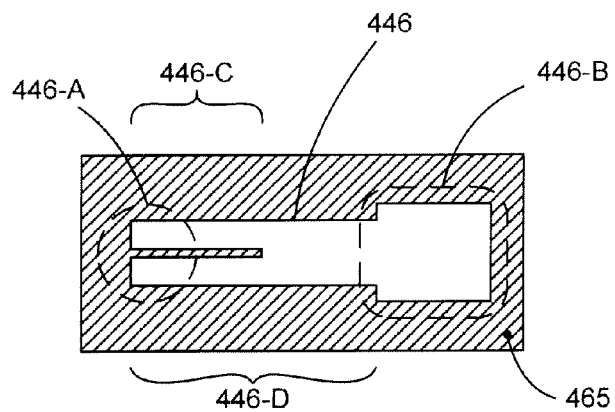
FIG. 5(A) is a top view showing a spring mask formed over a spring material film during the fabrication process shown in FIG. 4(C) according to another embodiment of the invention.

Referring to FIGS. 4(C) and 5(A)-5(I), an elongated spring mask 446 (e.g., photoresist) is then patterned over selected portions of stress-engineered film 465. Note that spring mask 446 is formed in the shape of the desired channel spring probe, and may include various tip, channel, and attachment region configurations. The well-characterized lithography processes that can be used to print spring mask 446 allow for significant flexibility in the actual geometry of spring mask 446. For example, FIG. 5(A) shows a plan view of spring mask 446, according to an embodiment of the invention. Spring mask 446 includes a probe tip region 446-A at one end, an attachment region 446-B at the other end, and a channel region 446-C between probe tip region 446-A and attachment region 446-B. Channel region 446-C is sized such that the resulting channel formed in the final channel spring probe provides the necessary capillary action on the liquid being collected by, stored in, or dispensed from the channel spring probe. FIG. 5(A) also indicates a release region 446-D, the portion of spring mask 446 corresponding to the portion of the channel spring probe to be released from substrate 440.

Figure 5B:
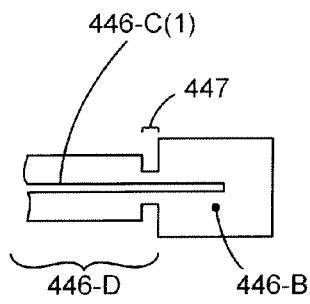
FIGS. 5(B), 5(C), 5(D), 5(E), 5(F), 5(G), and 5(H) are detail views of various regions of the spring mask shown in FIG. 5(A) according to various embodiments of the invention.
Figure 5C:
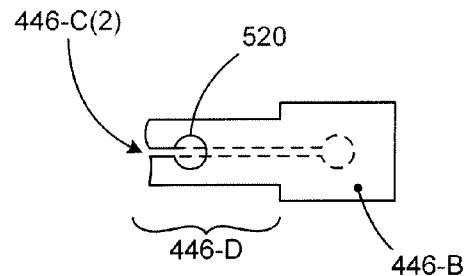

Note that while channel region 446-C is shown as overlapping with probe tip region 446-A, according to other embodiments of the invention, channel region 446-C can also extend into attachment region 446-B. For example, FIG. 5(B) shows a channel region 446-C(1) extending through release region 446-D into attachment region 446-B. An optional narrowed region 447 is included to provide a region of increased flexibility for the final channel spring probe (note that while narrowed region 447 is depicted where release region 446-D meets attachment region 446-B for explanatory purposes, narrowed region 447 can be located anywhere along release region 446-B). Various other modifications can be made to channel region 446-C, according to the intended usage of the final spring channel probe. For example, FIG. 5(C) shows a channel region 446-C(2) in accordance with another embodiment of the invention. The interior end of channel region 446-C(2) is connected to a reservoir region 520 for creating a reservoir feature in the final channel spring probe. Since the resulting reservoir feature will be wider than the channel width, the fluid holding capacity of channel region 446-C(2) will be increased. Note that while reservoir region 520 is shown as being located in release region 446-D, it can also be positioned in attachment region 446-B, as indicated by the dashed lines.

Figure 5D:
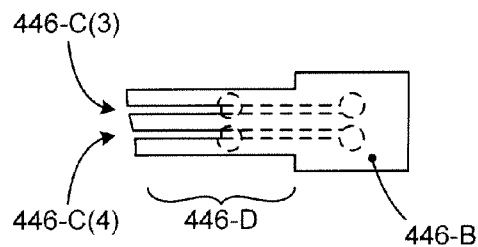

The invention also allows multiple channels to be formed in a channel spring probe. For example, FIG. 5(D) shows a portion of spring mask 446 having channel regions 446-C(3) and 446-C(4), in accordance with another embodiment of the invention. Note that like the channel regions described previously with respect to FIGS. 5(B) and 5(C), channels 446-C(3) and 446-C(4) can include reservoir features and/or can extend into attachment region 446-B, as indicated by the dashed lines.

Figure 5E:
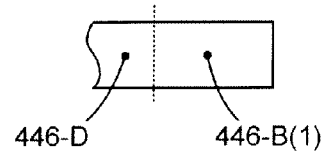
Figure 5F:
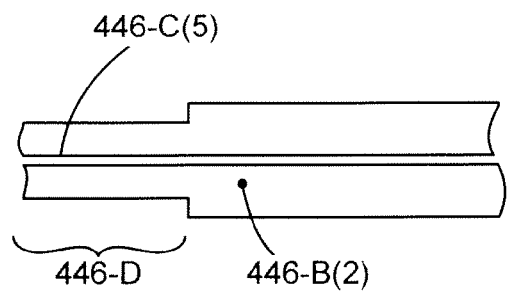

The same configuration flexibility applies to both attachment region 446-B and probe tip region 446-A shown in FIG. 5(A). For example, while depicted as a substantially rectangular region in FIGS. 5(A)-5(D), attachment region 446-B can take any number of forms. FIG. 5(E) shows an attachment region 446-B(1), in accordance with another embodiment of the invention. Attachment region 446-B(1) has the same width as release region 446-D, which will result in a straight-line (i.e., uniform width) channel spring probe having a uniform width. Various other attachment region configurations are possible, including, but not limited to, V-shaped, U-shaped, J-shaped, and L-shaped configurations. FIG. 5(F) shows an attachment region 446-B(2) that is enlarged to allow extended routing of channel region 446-C(5), thereby allowing both out-of-plane and in-plane fluid routing channels to be formed by a single lithography process step.

Figure 5G:
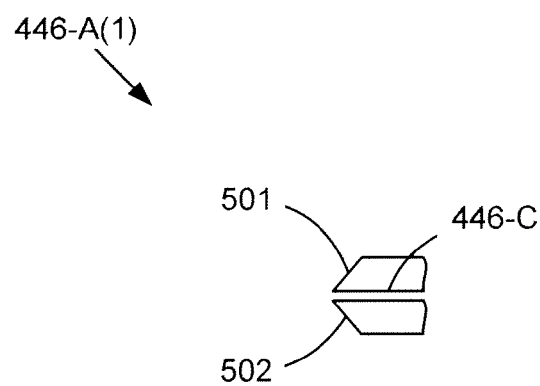

Similarly, probe tip region 446-A can take any configuration required to form the desired channel spring probe. For example, FIG. 5(G) shows a probe tip region 446-A(1) in accordance with another embodiment of the invention. In contrast to the blunt probe tip region 446-A shown in FIG. 5(A), probe tip region 446-A(1) includes chamfers 501 and 502 that provide a tapered tip on each side of channel region 446-C. This tapered tip configuration can reduce fluid travel along the (printing) edge of the resulting channel spring probe tip, thereby enabling the dispensing of finer fluid lines than would be possible with a similar channel spring probe having a flat tip configuration.

Figure 5H:
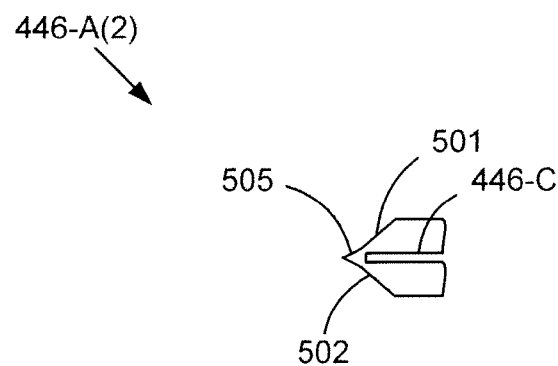

FIG. 5(H) shows a probe tip region 446-A(2), in accordance with another embodiment of the invention. Probe tip region 446-A(2) not only includes chamfers 501 and 502, but also includes a pointed tip 505 that closes off the end of channel region 446-C. By properly sizing pointed tip 505 and its distance from the end of channel region 446-C, fluid in the resulting channel spring probe could wick from the channel region to the apex of the sharp pointed tip, thereby allowing extremely fine fluid lines to be dispensed. According to an embodiment of the invention, channel region 446-C can end 1-3 µm or less from the apex of pointed tip 505.

Figure 4D:
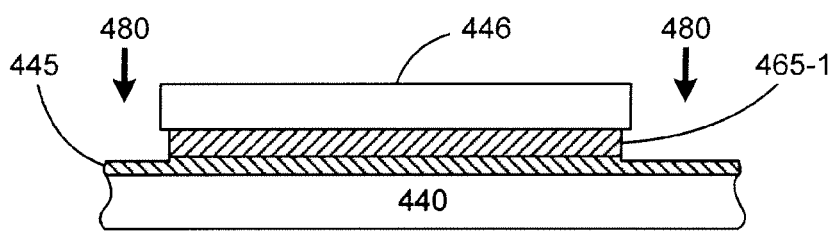

Returning to the channel spring probe fabrication process, FIG. 4(D) shows the exposed portions of stress-engineered film 465 surrounding spring mask 446 being etched using one or more etchants 480 to form a spring island 465-1. Note that this etching process is performed such that limited etching occurs in release layer 445 surrounding spring material island 465-1. In one embodiment, the etching step may be performed using a wet etch process to remove exposed portions of stress-engineered film 465—e.g., the use of a cerric ammonium nitrate solution to remove a MoCr spring metal layer. In another embodiment, anisotropic dry etching is used to etch both stress-engineered film 465 and the upper surface of the exposed portion of release layer 445. This embodiment may be performed, for example, with Mo spring metal, and Si or Ti release layers. Mo, Si and Ti all etch in reactive fluorine plasmas. An advantage of dry etching the spring material film is that it facilitates finer features and sharper tipped channel spring probes. Materials that do not etch in reactive plasmas may still be etched anisotropically by physical ion etching methods, such as argon ion milling. In yet another possible embodiment, the etching step can be performed using the electro-chemical etching process described in IBM J. Res. Dev. Vol. 42, No. 4, page 655 (Sep. 4, 1998), which is incorporated herein by reference. Many additional process variations and material substitutions are therefore possible and the examples given are not intended to be limiting.

Figure 4E:
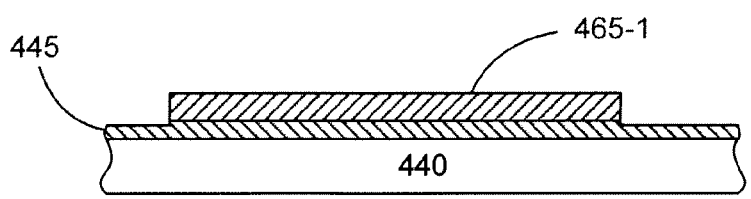
Figure 4F:
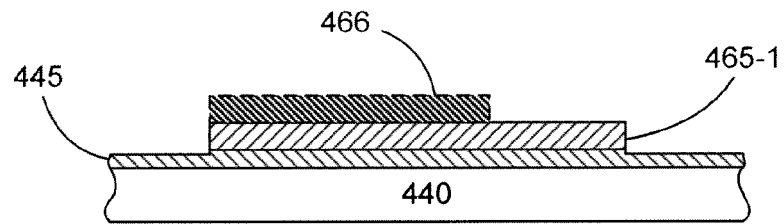

FIG. 4(E) shows spring material island 465-1 and release layer 445 after spring mask 446 (FIG. 4(D)) is removed. At this point, optional channel area patterning 466 may be formed on spring material island 465-1, as indicated in FIG. 4(F). Channel area patterning 466 allows secondary channel features to be formed on spring material island 465-1. Note that if channel features have already been patterned into spring island 465-1, optional channel area patterning 466 would not be required, although secondary channel features could be used to modify or add to the features integrated into spring island 465-1. Note further that this additional channel area patterning can alternatively be performed after the appropriate portion of spring material island 465-1 is released from substrate 440 (to be discussed with respect to FIG. 4(H)).

Figure 4G:
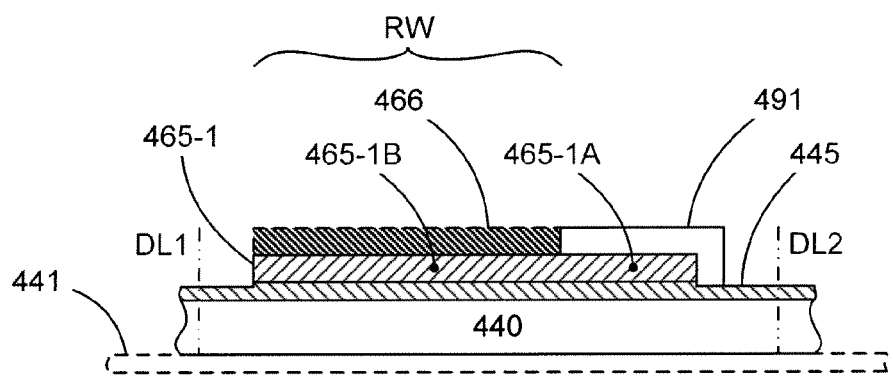

In FIG. 4(G), a release mask 450 is formed on a first portion 465-1A of spring material island 465-1. Release mask 491 defines a release window RW, which exposes a second portion 465-1B of spring material island 465-1 and surrounding portions release layer 445. Release mask 491 may also serve as a strapping structure to further secure first portion 465-1A to substrate 440. In one embodiment of the invention, release mask 491 is formed using photoresist. In other embodiments of the invention, a suitable metal or epoxy may be used. Note that according to other embodiments of the invention, release mask 491 could be eliminated through appropriate patterning of release layer 445 and/or first portion 465-1A of spring material island 465-1.

At this point, substrate 440 can be diced (for example along dice lines DL1 and DL2) to prevent damage to the subsequently lifted structures (i.e., spring beam 460 shown in FIG. 4(H)). An optional sticky dicing tape 441 could be used to prevent shifting of the substrate during and after dicing (i.e., the dicing blade only cuts through substrate 440 (and the overlying portions of release layer 445) but not through the underlying sticky tape 441). Alternatively, dicing could be performed after release of portion 465-1B from substrate 440. In such a case, if protection of the released beams during dicing were desired, beam passivation using resist or wax could be used.

Figure 4H:
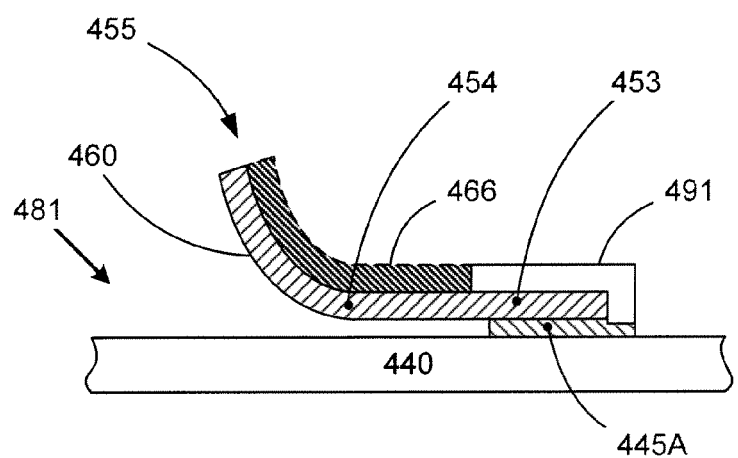

In FIG. 4(H), a release etchant 481 (e.g., a buffered oxide etch) is used to selectively remove a portion of release layer 445 from beneath the exposed portion of spring island 465-1 (i.e., second portion 465-1B) and foLm a curved spring beam 460. Specifically, removal of the exposed release material causes cantilever portion 454 of spring beam 460 to curve away from substrate 440 in response to the internal stress variations established during the formation of the stress engineered film (discussed above). Note that fixed end 453 of spring beam 460 remains secured to substrate 440 by release material (support) portion 445A, which is protected by release mask 491. Alternatively, release mask 491 may be removed from fixed end 453 of spring beam 460 after release. Optional channel area patterning 466 can be formed on spring beam 460 at this point (i.e., after release) if it has not been previously formed (e.g., in FIG. 4(F)). Then, if channel area patterning 466 is present, additional deposition process(es) can be performed to form the actual channel structure 467 of the completed channel spring probe 450 shown in FIG. 4(I) (as noted previously, the channel features could be defined within (i.e., integrated into) spring beam 460, in which case spring probe 450 would not require channel structure 467).

Figure 6A:
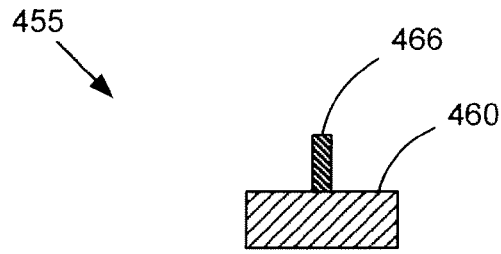
FIGS. 6(A), 6(B), and 6(C) are frontal views showing a process for forming a channel on the surface of a spring beam according to another embodiment of the invention.
Figure 6B:
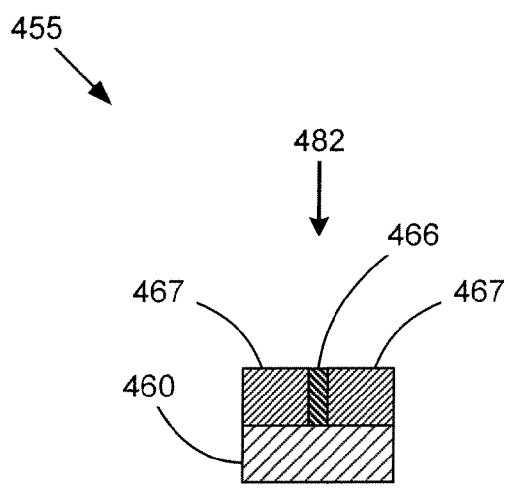
Figure 6C:
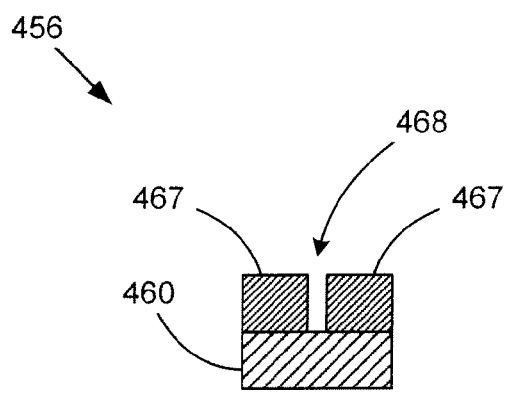

The formation of channel structure 467 is demonstrated in greater detail in FIGS. 6(A)-6(C). FIG. 6(A) shows a frontal (head-on) view of intermediate probe tip 455 shown in FIG. 4(H), with channel area patterning 466 overlying a desired portion of spring beam 460. Channel area patterning 466 can comprise a hard mask (e.g., hard resist) or any other material that can be removed without removing the subsequently foamed channel structure. In FIG. 6(B), channel structure 467 is formed on the portions of spring beam 460 not masked by channel area patterning 466, and a resist strip 482 is applied to remove channel area patterning 466. A frontal view of the resulting probe tip 456 (from FIG. 4(I)) is shown in FIG. 6(C), with the gap formerly occupied by channel area patterning 466 becoming channel 468. Note that various other geometries for channel area patterning 466 and channel structure 467 are possible, as will be described with respect to FIGS. 8(B)-8(H). According to an embodiment of the invention, channel structure 467 can be electroplated onto spring beam 460. According to other embodiments of the invention, various other materials (e.g., oxides, nitrides, organic materials (carbides), etc.) and processes (e.g., sputtering, evaporation, chemical vapor deposition (CVD), spinning, etc.) can be used to form channel structure 467. Note that channel structure (467) can be formed prior to the release of spring beam 460 from substrate 440 (i.e., on spring island 465-1 shown in FIG. 4(G)), although the channel structure would generate beam loading that could reduce the release height of spring beam 460.

Returning to FIG. 4(I), according to an embodiment of the invention, substrate 440 can include integrated fluidic paths, as indicated by optional fluidic path 444. Channel spring beams can be formed on a substrate that already includes such integrated fluidic paths to simplify the construction of advanced fluidic routing systems. For example, an optional support structure 442 can be attached to substrate 440 to provide additional mechanical support and/or interface elements. Support structure 442 can include an optional fluid reservoir 443 for supplying channel spring probe 450 with liquid. In such a situation, substrate 440 could include a preformed integrated via (fluidic path 444), that would couple the channel of channel spring probe 450 with reservoir 443 of support structure 442. Fluid reservoir 443 could then either supply liquid to, or store liquid gathered by, spring channel probe 450.

According to another embodiment of the invention, an optional protective coating 461 (indicated by a dotted line) such as paralyne or oxide can also be formed over any exposed portions of spring beam 460 (and channel structure 467). According to another embodiment of the invention, an optional secondary tip 469 can be formed at, or attached to, the end of spring beam 460 using methods like FIB, EBD, carbon-nanotube growth, by etching a material deposited on the surface of spring beam 460 prior to release, or by postrelease attachment. Various secondary tip configurations are described more fully in co-owned, co-pending U.S. patent application Ser. No. 10/136,258 entitled "Scanning Probe System with Spring Probe And Actuation/Sensing Structure filed Apr. 30, 2002 by Thomas Hantschel et al., herein incorporated by reference.

Figure 4I:
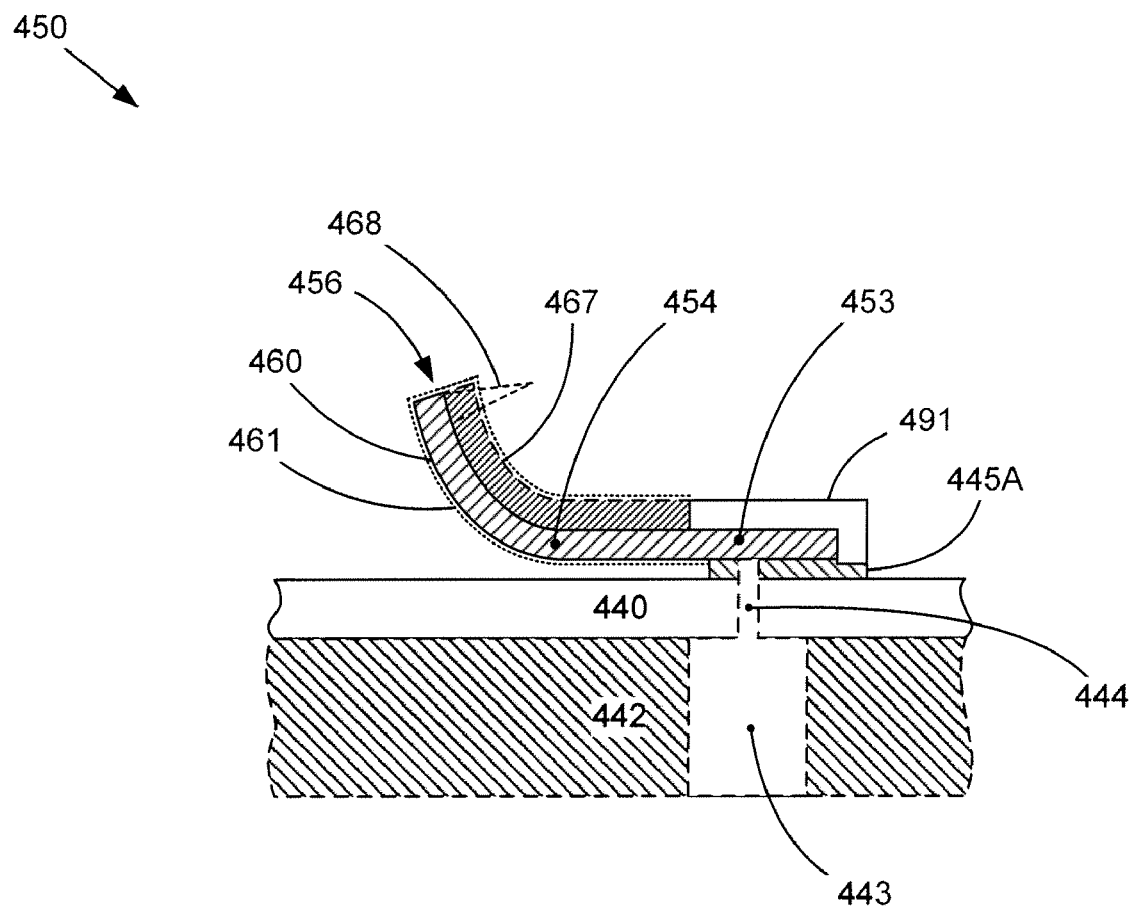
Figure 7A:
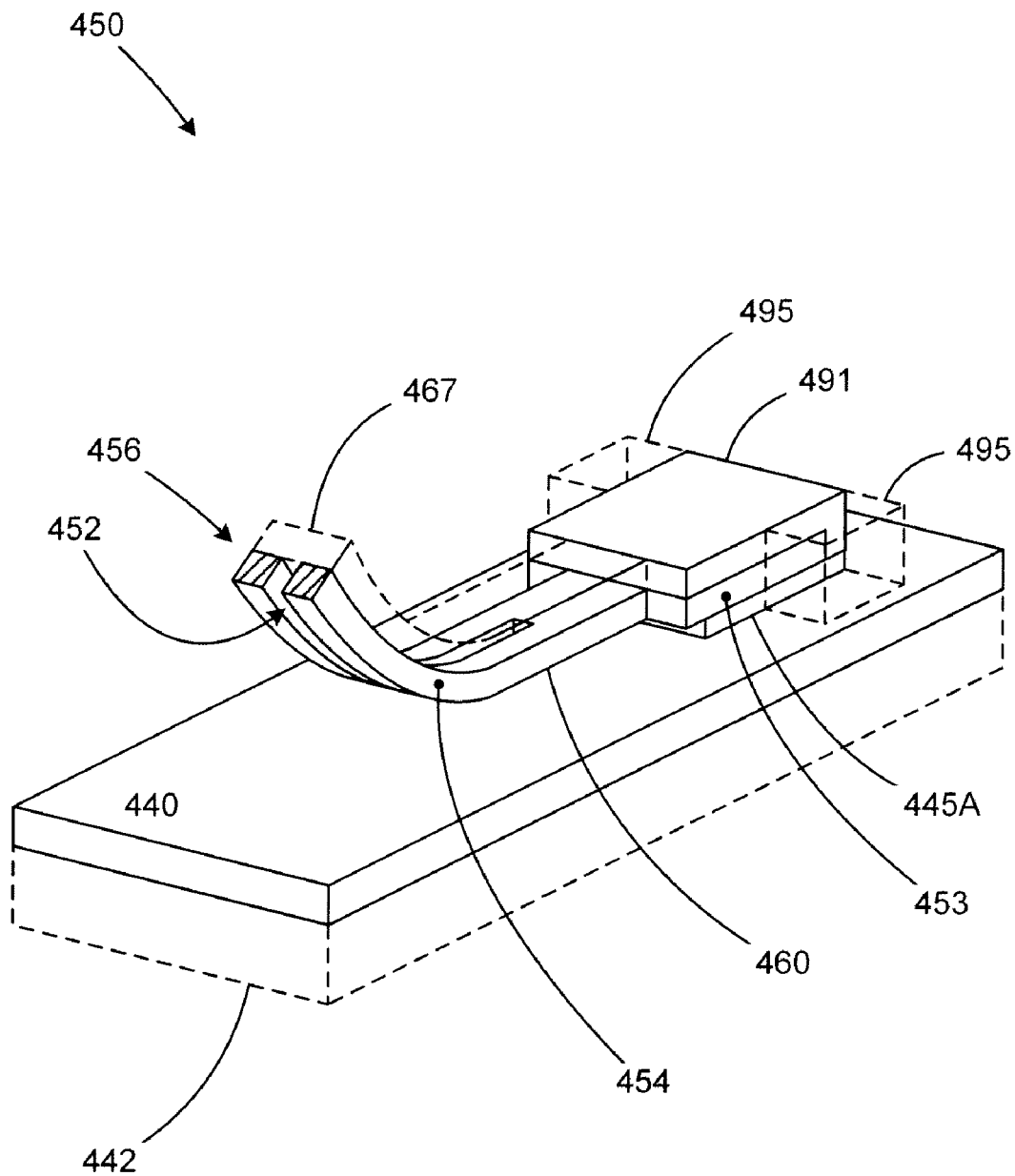
FIG. 7(A) is a perspective view showing a channel spring probe according to another embodiment of the invention.

FIG. 7(A) shows a perspective view of completed channel spring probe 450 from FIG. 4(I). Channel spring probe 450 can now be used in any fluidic system, such as microarraying system 300A shown in FIG. 3(A), DPN system 300B shown in FIG. 3(B), and fluidic circuit 300C shown in FIG. 3(C). Note that channel spring probe 450 also includes optional operational modules 495 that can be formed after or in conjunction with the process described with respect to FIGS. 4(A)-4(I). Operational modules can be adjacent to or attached to spring beam 460, and can comprise various structures for providing additional functionality to channel spring probe 450, such as actuators, heaters, temperature sensors, stress sensors, optical detectors, deflection sensors, chemical sensors, and integrated electronic circuits (for controlling actuation, signal processing, etc.). For example, each of the channel spring probes in an array of channel spring probes (such as microarray 330A shown in FIG. 3(A) or micropen assembly 330B shown in FIG. 3(B)) can include an actuator and a deflection sensor to help align the tips of all the channel spring probes.

Figure 9A:
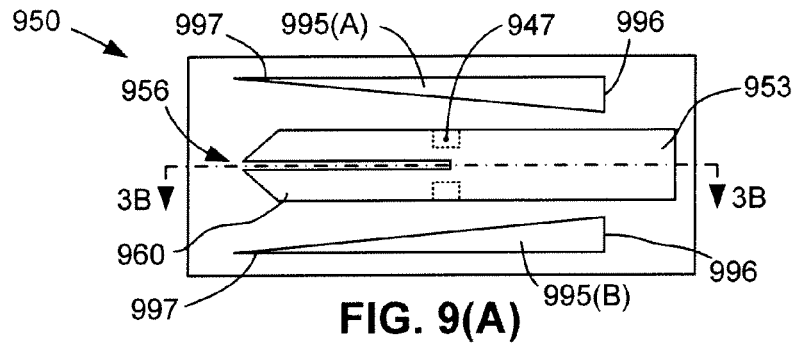
FIGS. 9(A), 9(B), and 9(C) are top, cross-sectional side, and end views, respectively showing a channel spring probe incorporating actuation electrodes according to an embodiment of the present invention.
Figure 9B:
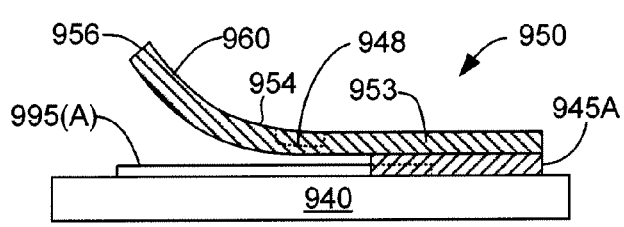
Figure 9C:
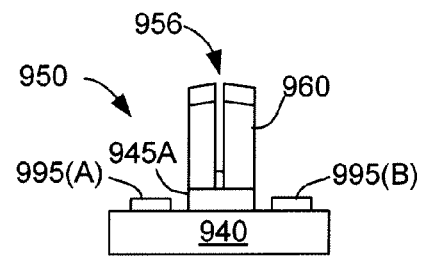

For example, FIGS. 9(A) through 9(C) are top, cross-sectional side, and end views, respectively, showing a channel spring probe 950 incorporating an actuation electrode structure including a first elongated electrode portion 995(A) and a second elongated electrode portion 995(B) formed on substrate 940 and extending parallel to and offset from the sides of spring beam 960. Each of elongated electrode portions 995(A) and 995(B) has a tapered shape including a relatively wide portion 996 located adjacent to fixed end 953 of spring beam 960, and a relatively narrow portion 997 located adjacent to probe tip 956. The present inventors have determined that tapered electrode portions 995(A) and 995(B) reduce forces exerted along the length of spring beam 960 due to the diminished field strength (along its length) inherent to the tapered electrode design, thereby facilitating a stable "rolling/zipper" motion of spring beam 960 (described below with reference to FIGS. 10(A) through 10(C). Further, by offsetting tapered electrode portions 995(A) and 995(B) from (i.e., mounting on opposite sides of) spring beam 960, the actuation voltage needed to achieve full deflection of probe tip 956 is minimized. Other electrostatic actuation electrode patterns are described in co-owned, co-pending U.S. patent application Ser. No. 10/136,258 entitled "Scanning Probe System with Spring Probe And Actuation/Sensing Structure filed Apr. 30, 2002 by Thomas Hantschel et al. Note that spring beam 960 can also includes an optional narrowed portion 947, as indicated in FIG. 9(A), to reduce the force required to deflect spring beam 960. Alternatively, spring beam 960 can include an enhanced flexibility portion 948, as indicated in FIG. 9(B) to provide a similar effect. Note further that enhanced flexibility portion 948 can be formed in various ways, including locally thinning spring beam 960 or locally integrating a softer material into spring beam 960. Note further that narrowed portion 947 in FIG. 9(A) and enhanced flexibility portion 948 in FIG. 9(B) can be located anywhere along cantilever portion 954.

Figure 10A:
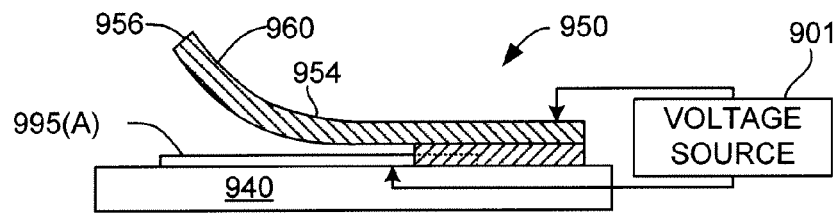
FIGS. 10(A), 10(B), and 10(C) are cross-sectional side views depicting actuation of the channel spring probe of FIG. 9(B).
Figure 10B:
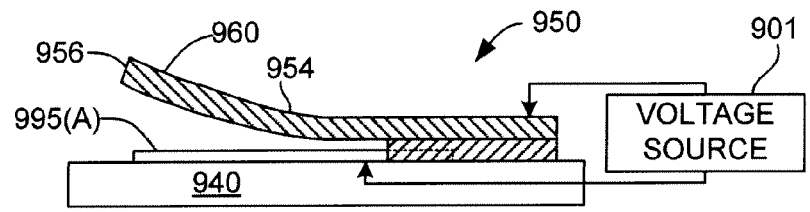
Figure 10C:
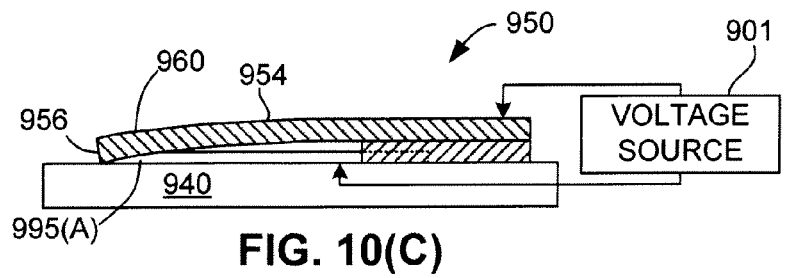

FIGS. 10(A) through 10(C) are cross-sectional side views illustrating the "rolling/zipper" motion of spring beam 960. Referring to FIG. 4(A), when a relatively small voltage signal is applied by a voltage source 901 to spring beam 960 and elongated electrode portions 995(A) and 995(B), cantilever portion 954 remains substantially in its unbiased position (i.e., bent into a shape determined by the channel spring probe design). As shown in FIG. 10(B), as the applied voltage generated by voltage source 901 increases, cantilever portion 954 is actuated towards substrate 940 and straightened, thereby "unrolling" spring beam 960. As shown in FIG. 10(C), when the applied voltage generated by voltage source 901 reaches a sufficiently large value, spring beam 960 is further unrolled until tip 956 abuts substrate 940. This actuation capability can substantially improve the functionality of devices incorporating channel spring probes. For example, in microarray 330A shown in FIG. 3(A), individual channel spring probes 350A can be "turned off" by actuating them towards substrate 340A. In a similar manner, individual channel spring probes in micropen assembly 330B shown in FIG. 3(B) can be turned off and on via actuation towards (and away from) substrate 340B.

Figure 7B:
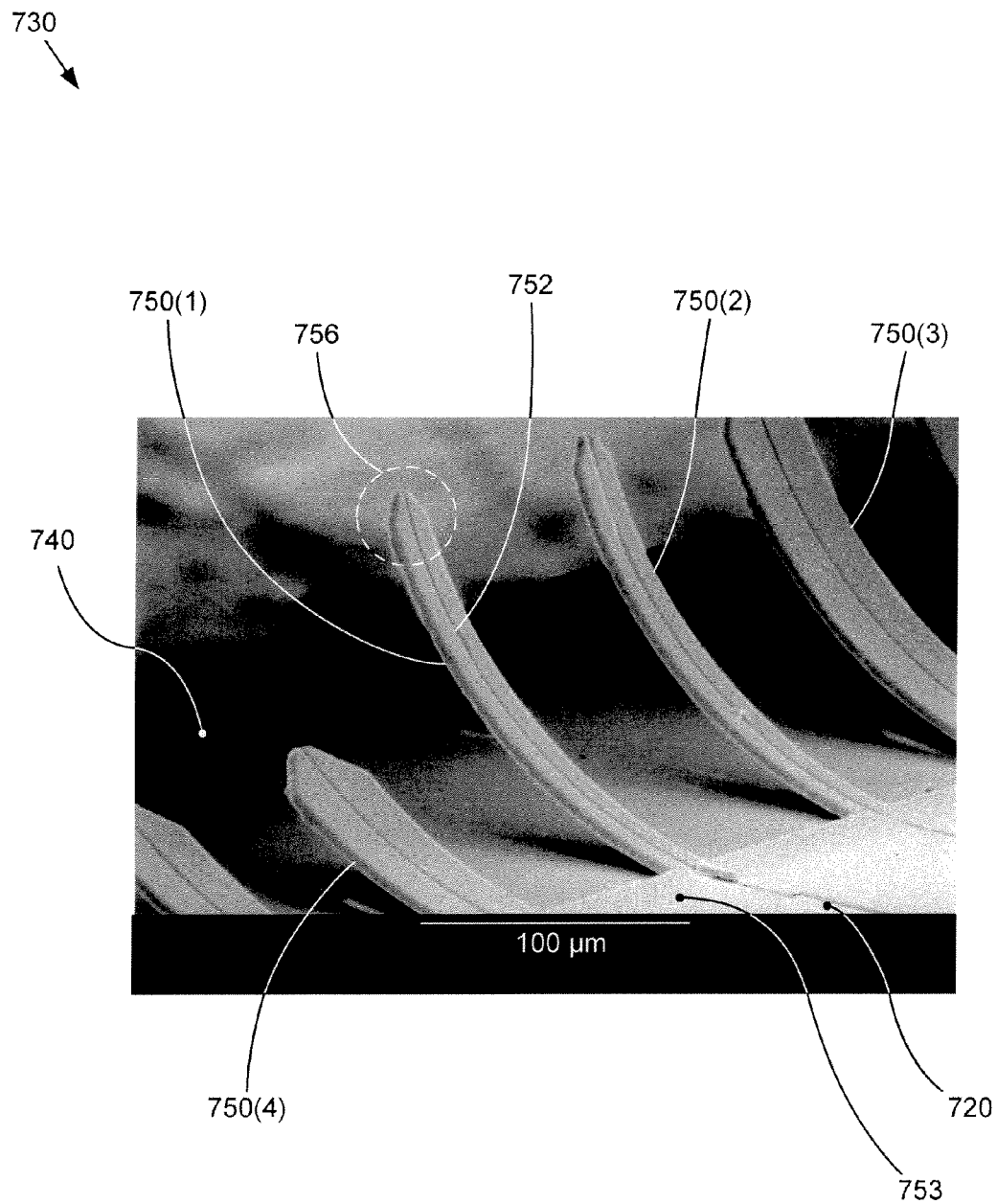
FIG. 7(B) is an enlarged photograph showing an actual channel spring probe array produced in accordance with the fabrication process described with reference to FIGS. 4(A) through 4(I)

FIG. 7(B) is an enlarged photograph showing an actual channel spring probe array 730 that was produced by the present inventors utilizing the fabrication process described above. Channel spring probe array 730 includes channel spring probes 750(1), 750(2), 750(3), and 750(4) (among others not labeled for clarity) curving away from a substrate 740. Each of channel spring probes 750(1)-750(4) is attached to substrate 740 at a fixed end 753 and includes a channel as previously described with respect to FIG. 7(A). For example, channel spring probe 750(1) includes a channel 752 that extends completely through a tapered probe tip 756 (such as defined by probe tip region 446-A(1), described with respect to FIG. 5(H)). Note also that channel 752 extends into fixed end 753 and ends in a reservoir 753, as was previously described with respect to FIGS. 5(B) and 5(C).

Figure 8A:
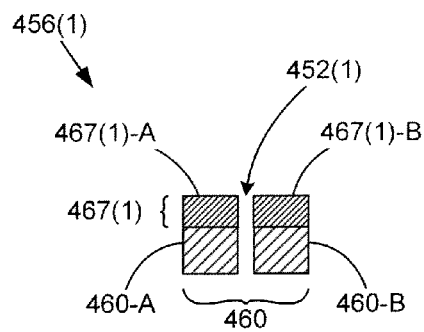
FIGS. 8(A), 8(B), 8(C), 8(D), 8(E), and 8(F) are frontal views of channel spring probe tips according to various embodiments of the invention.

Returning to FIG. 7(A), note that channel 452 in spring beam 460 includes a channel 452 that could be supplemented or replaced by channel features in optional channel structure 467 (shown simply as a dashed volume for clarity). Therefore, probe tip 456 can take a variety of forms. For example, FIG. 8(A) shows a frontal view of a probe tip 456(1) in accordance with an embodiment of the invention. Probe tip 456(1) includes a channel 452(1) defined by both spring beam 460 and channel structure 467(1). Channel structure portions 467(1)-A and 467(1)-B are positioned directly over spring beam portions 460-A and 460-B, respectively, thereby increasing the height of the channel included in spring beam 460.

Figure 8B:
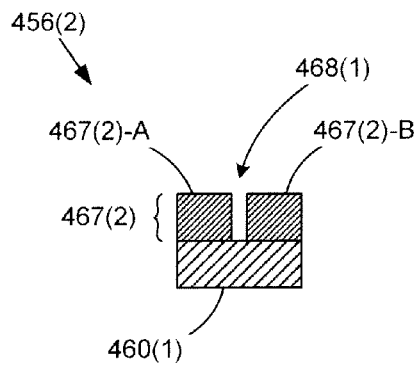

FIG. 8(B) shows a frontal view of a probe tip 456(2) in accordance with another embodiment of the invention. Rather than adding to an existing channel in the spring beam, channel structure 467(2) in probe tip 456(2) is formed on a spring beam 460(1) that does not include any channel feature (i.e., a "blank" spring beam). A channel 468(1) is therefore defined entirely by channel structure portions 467(2)-A and 467(2)-B.

Figure 8C:
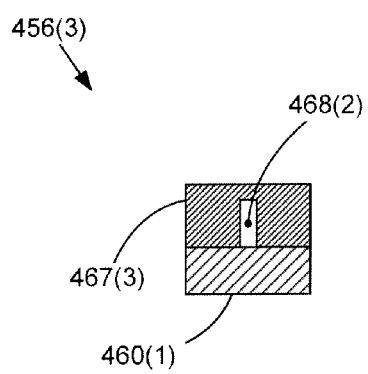

FIG. 8(C) shows a frontal view of a probe tip 456(3) in accordance with another embodiment of the invention. In probe tip 456(3), channel structure 467(3) formed on blank spring beam 460(1) defines a fully enclosed channel 468(2). Channel structure 467(3) could be formed, for example, by completely plating over channel area patterning such as shown in FIG. 6(A). Since channel 468(2) is enclosed on all sides, fluid access/egress is only possible through the ends of channel 468(2), which can minimize the risks of fluid contamination and provide more secure transport for liquids held in channel 468(2).

Figure 8D:
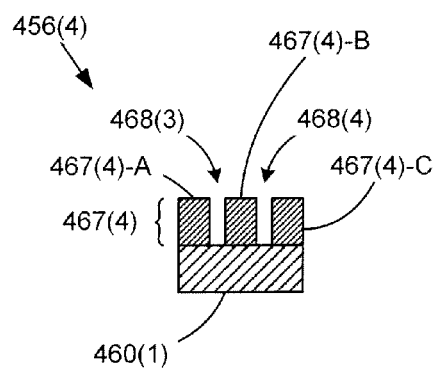

FIG. 8(D) shows a frontal view of a probe tip 456(4) in accordance with another embodiment of the invention. Channel structure 467(4) defines channels 468(3) and 468(4) by positioning channel structure portions 467(4)-A, 467(4)-B, and 467(4)-C on blank spring beam 460(1). Note that this principle may be used to form any number of channels in a channel spring probe.

Figure 8E:
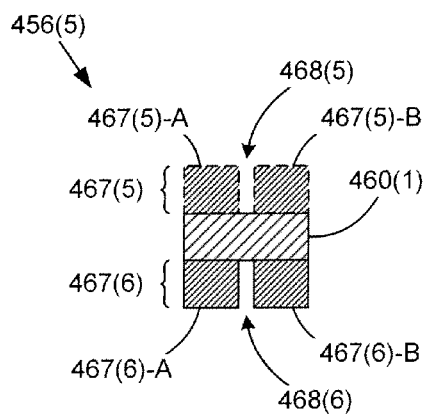

FIG. 8(E) shows a frontal view of a probe tip 456(5) that includes multiple channels in accordance with another embodiment of the invention. Probe tip 456(5) includes channel structures 467(5) and 467(6) on the top and bottom surfaces, respectively, of blank spring beam 460(1). Channel structure 467(5) includes channel structure portions 467(5)-A and 467(5)-B that define a channel 468(5) on the top surface of spring beam 460(1), while channel structure 467(6) includes channel structure portions 467(6)-A and 467(6)-B that define a channel 468(6) on the bottom surface of spring beam 460(1). Note that probe tip 456(5) could include only channel structure 467(6) (as indicated by the dashed lines used for channel structure 467(5)), thereby providing a channel (i.e., channel 468(6)) on only the bottom surface of spring beam 460(1).

Figure 8F:
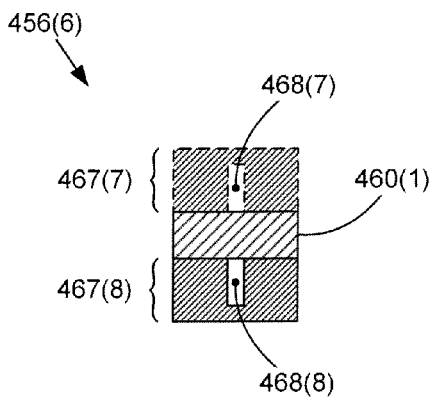

FIG. 8(F) shows a frontal view of a probe tip 456(6) that includes multiple enclosed channels in accordance with another embodiment of the invention. Probe tip 456(6) includes channel structures 467(7) and 467(8) on the top and bottom surfaces, respectively, of blank spring beam 460(1), thereby defining fully enclosed channels 468(7) and 468(8), respectively. Note that probe tip 456(6) could include only channel structure 467(8) (as indicated by the dashed lines used for channel structure 467(7)), thereby defining a channel (i.e., channel 468(8)) on only the bottom surface of spring beam 460(1).

Figure 8G:
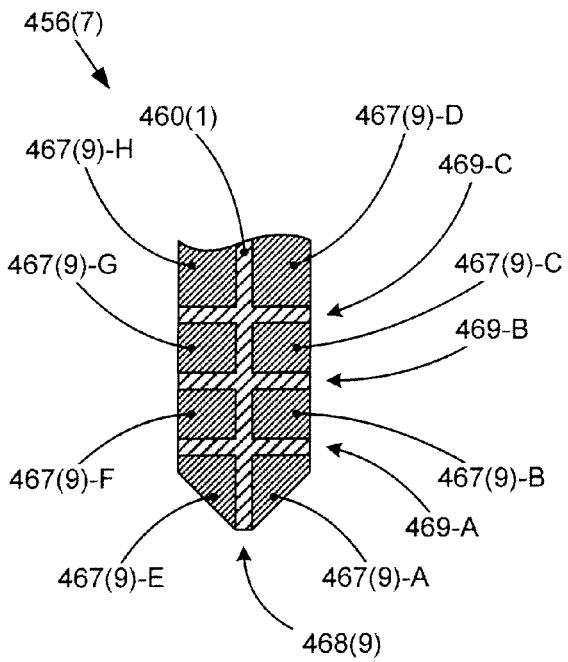
FIGS. 8(G), 8(H), and 8(I) are top views of channel spring probe tips according to various embodiments of the invention
Figure 8H:
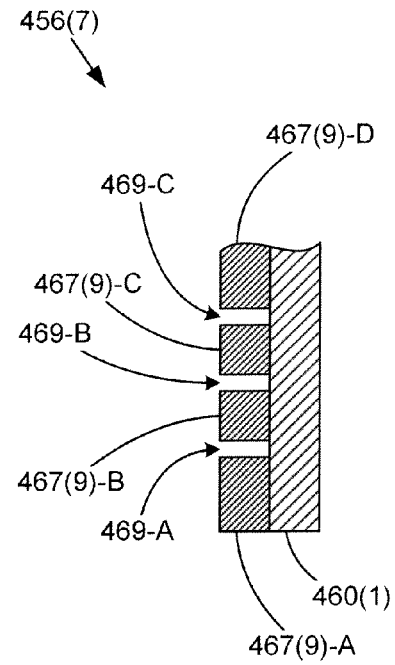
Figure 8I:
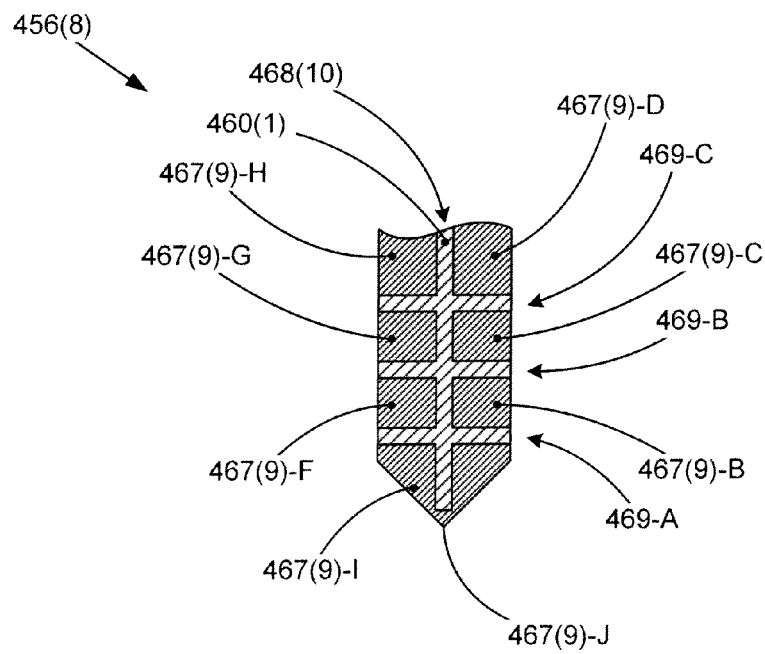

Note that channel features created by the aforementioned types of channel structures can include any reservoir features (such as those described with respect to FIGS. 5(C) and 5(D)) or other formations that are desired on the surface of the spring beam. For example, FIG. 8(G) shows a plan view of a probe tip 456(7) in accordance with another embodiment of the invention. Probe tip 456(7) includes channel structure portions 467(9)-A through 467(9)-H, arranged on blank spring beam 460(1) to define a channel 468(9) and cross channels 469-A, 469-B, and 469-C. Cross channels 469-A, 469-B, and 469-C are perpendicular to channel 468(9) and span the width of spring beam 460(1). Channel structure portions 467(9)-A and 467(9)-E are angled such that probe tip 467(7) has a substantially tapered end. Such a configuration can, for example, be used in puncture applications, with cross channels 469-A, 469-B, and 469-C providing increased fluid delivery capacity. FIG. 8(H) provides a side view of probe tip 456(7), showing cross channels 469-A, 469-B, and 469-C spaced along the surface of spring beam 460(1).

FIG. 8(H) shows a plan view of a probe tip 456(8) having cross channels in accordance with another embodiment of the invention. Probe tip 456(8) is substantially similar to probe tip 456(7) shown in FIGS. 8(G) and 8(H), except that channel structure portions 467(9)-A and 467(9)-E in probe tip 456(7) are replaced with a single channel structure portion 467(9)-I that includes a pointed tip 467(9)-J. Pointed tip 467(9)-J closes off channel 468(10) at the end of probe tip 456(8). As described previously with respect to FIG. 5(H), pointed tip 467(9)-J can still allow fluid transport to and from channel 468(10), while providing additional stability and piercing capability to probe tip 456(8).

Although the present invention has been described in connection with several embodiments, it is understood that this invention is not limited to the embodiments disclosed, but is capable of various modifications that would be apparent to one of ordinary skill in the art. For example, a spring beam (or even a bond wire, such as produced by FormFactor, Inc.) could be plated on all sides and then etched away, leaving only the plating as an out-of-plane tube. Thus, the invention is limited only by the following claims.

The invention claimed is:

1. A method for forming a fluidic conduit, the method comprising:
   forming a plurality of spring material islands in an array pattern on a release material layer such that each of the plurality of spring material islands has an internal stress gradient in a direction normal to the release material layer, wherein each of the plurality of spring material islands is disposed on a corresponding portion of the release material layer and includes a single-piece construction having a fixed portion and a cantilever portion, wherein the cantilever portion of each said spring material island has a fixed end integrally attached to said fixed portion;
   removing a first portion of the release material layer from beneath the cantilever portion of each of the plurality of spring material islands, thereby causing the cantilever portion to assume a curvature bending away from a second portion of the release layer due to the internal stress gradient, whereby the fixed end of each said spring material island remains connected to the substrate by an associated said second portion of the release material layer; and
   defining a first channel in the cantilever portion of each of the plurality of spring material islands for carrying fluid along the cantilever portion of each said spring material island, the first channel running substantially parallel to the curvature of the cantilever portion and being formed such that each said spring material island maintains said single-piece construction.

2. The method of claim 1, further comprising masking a fixed end portion of each said spring material island.

3. The method of claim 1, further comprising depositing said release material layer on a substrate, wherein the release material layer comprises one or more of silicon (Si), silicon-nitride (SiNx), silicon-oxide (SiOx), and titanium (Ti).

4. The method of claim 1, wherein forming the plurality of spring material islands in an array pattern comprises:
   forming a spring material film on the release material layer, the spring material film having the internal stress gradient in a direction normal to the release material layer; and
   etching the spring material film to form the plurality of spring material islands in an array pattern.

5. The method of claim 4, wherein forming the spring material film comprises sputtering the spring material film on a wafer formed from the release material.

6. The method of claim 4, wherein forming the spring material film comprises sputtering one or more metals selected from molybdenum (Mo), tungsten (W), titanium (Ti), chromium (Cr), and nickel (Ni) while altering process parameters such that portions located adjacent to the release material layer have a higher internal compressive stress than portions located further from the release material layer.

7. The method of claim 4, wherein etching the spring material film comprises:
   forming a first mask on the spring material film; and
   etching exposed portions of the spring material film located around the first mask.

8. The method of claim 7, wherein defining the first channel comprises including a first elongated slot in the first mask such that each said spring material island includes a first in-plane channel feature in the cantilever portion, the first in-plane channel feature being substantially parallel to the cantilever portion, the first in-plane channel feature becoming the first channel after the removal of the release material layer from beneath the unmasked cantilever portion of each said spring material island.

9. The method of claim 8, wherein the first mask includes a tapered end such that the spring material island includes an in-plane tapered tip shaped by the tapered end.

10. The method of claim 8, wherein the first in-plane channel feature extends into the fixed end portion of each said spring material island.

11. The method of claim 8, further comprising defining a second channel for carrying fluid along the cantilever portion of each said spring material island, the second channel running substantially parallel to the curvature of the cantilever portion, wherein defining the second channel comprises including a second elongated slot in the first mask such that each said spring material island includes a second in-plane channel feature in the cantilever portion, the second in-plane channel feature being substantially parallel to the cantilever portion, wherein after removal of the release material layer from beneath the unmasked cantilever portion of each said spring material island, the second in-plane channel feature becomes the second channel.

12. The method of claim 9, wherein the first elongated slot extends completely through the tapered end.

13. The method of claim 9, wherein the tapered end terminates in a pointed tip, and wherein the first elongated slot extends into the tapered end and ends before the pointed tip.

14. A method for forming a fluidic conduit, the method comprising:
   forming a plurality of spring material islands in an array pattern on a release material layer such that each of the plurality of spring material islands has an internal stress gradient in a direction normal to the release material layer;
   removing a first portion of the release material layer from beneath a cantilever portion of each of the plurality of spring material island, thereby causing the cantilever portion to assume a curvature bending away from a second portion of the release layer due to the internal stress gradient; and
   defining a first channel for carrying fluid along the cantilever portion of each said spring material island, the first channel running substantially parallel to the curvature of the cantilever portion,
   wherein defining the first channel comprises:
   forming a first channel structure pattern on a first surface of the cantilever portion, the first channel structure pattern covering a first channel portion on the first surface of the cantilever portion;
   depositing channel structuring material on exposed portions of the first surface located around the first channel portion; and
   removing the first channel structure pattern, thereby revealing the first channel.

15. The method of claim 14, wherein the first channel structure pattern comprises a hard resist, and wherein removing the first channel structure pattern comprises applying a resist strip.

16. The method of claim 14, wherein depositing channel structuring material comprises forming a metal plating on the cantilever portion.

17. The method of claim 14, wherein the channel structuring material covers the first channel portion.

18. The method of claim 14, further comprising defining a second channel for carrying fluid along the cantilever portion of each said spring material island, the second channel running substantially parallel to the curvature of the cantilever portion, wherein defining the second channel comprises:
   forming a second channel structure pattern on the first surface of the cantilever portion, the second channel structure pattern covering a second channel portion on the first surface of the cantilever portion;
   depositing channel structuring material on exposed portions of the first surface located around the second channel portion; and
   removing the second channel structure pattern, thereby revealing the second channel.

19. The method of claim 14, further comprising defining a second channel for carrying fluid along the cantilever portion of each said spring material island, the second channel running substantially parallel to the curvature of the cantilever portion, wherein defining the second channel comprises:
   forming a second channel structure pattern on a second surface of the cantilever portion, the second channel structure pattern covering a second channel portion on the first surface of the cantilever portion, the first surface of the cantilever portion facing away from the release material layer and the second surface of the cantilever portion facing towards the release material layer;
   depositing channel structuring material on exposed portions of the second surface located around the second channel portion; and
   removing the second channel structure pattern, thereby revealing the second channel.

* * * * *